(12) United States Patent
Moore (10) Patent No.: US 11,278,396 B2
(45) Date of Patent: Mar. 22, 2022

(54) TRANSCATHETER MITRAL VALVE DESIGN

(71) Applicant: St. Jude Medical, Cardiology Division, Inc., St. Paul, MN (US)

(72) Inventor: Brandon Moore, Minneapolis, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 357 days.

(21) Appl. No.: 15/908,880

(22) Filed: Mar. 1, 2018

(65) Prior Publication Data

US 2018/0250128 A1 Sep. 6, 2018

Related U.S. Application Data

(60) Provisional application No. 62/466,423, filed on Mar. 3, 2017.

(51) Int. Cl.
*A61F 2/24* (2006.01)

(52) U.S. Cl.
CPC .......... *A61F 2/2412* (2013.01); *A61F 2/2418* (2013.01); *A61F 2/2427* (2013.01); *A61F 2/2454* (2013.01); *A61F 2/2457* (2013.01); *A61F 2220/0016* (2013.01); *A61F 2230/0008* (2013.01); *A61F 2230/0013* (2013.01); *A61F 2230/0023* (2013.01); *A61F 2230/0054* (2013.01); *A61F 2250/0037* (2013.01); *A61F 2250/0063* (2013.01)

(58) Field of Classification Search
CPC ............. A61F 2/82; A61F 2/24; A61F 2/2412
See application file for complete search history.

(56) References Cited

U.S. PATENT DOCUMENTS

| | | | |
|---|---|---|---|
| 3,657,744 A | 4/1972 | Ersek | |
| 4,275,469 A | 6/1981 | Gabbay | |
| 4,491,986 A | 1/1985 | Gabbay | |

(Continued)

FOREIGN PATENT DOCUMENTS

| | | |
|---|---|---|
| DE | 19857887 A1 | 7/2000 |
| DE | 10121210 A1 | 11/2002 |

(Continued)

OTHER PUBLICATIONS

International Search Report including Written Opinion for PCT/US2018/020370 dated May 17, 2018.

(Continued)

*Primary Examiner* — Matthew W Schall
(74) *Attorney, Agent, or Firm* — Lerner, David, Littenberg, Krumholz & Mentlik, LLP (57) ABSTRACT

A prosthetic mitral valve includes a collapsible and expandable stent extending from an inflow end to an outflow end. A collapsible and expandable valve assembly is disposed within the stent. The valve assembly includes a plurality of anterior leaflets and one posterior leaflet. The posterior leaflet has a larger surface area than any of the anterior leaflets. When implanted in the native mitral valve annulus, the smaller size of the anterior leaflets and the corresponding smaller size of an anterior portion of the stent reduce the likelihood of interference with blood flowing through the native aortic valve, while also reducing the likelihood of ventricular fibrillation.

11 Claims, 8 Drawing Sheets

(56) References Cited

U.S. PATENT DOCUMENTS

| | | | |
|---|---|---|---|
| 4,759,758 A | 7/1988 | Gabbay | |
| 4,878,906 A | 11/1989 | Lindemann et al. | |
| 4,922,905 A | 5/1990 | Strecker | |
| 4,994,077 A | 2/1991 | Dobben | |
| 5,411,552 A | 5/1995 | Andersen et al. | |
| 5,415,664 A | 5/1995 | Pinchuk | |
| 5,480,423 A | 1/1996 | Ravenscroft et al. | |
| 5,843,167 A | 12/1998 | Dwyer et al. | |
| 5,855,601 A | 1/1999 | Bessler et al. | |
| 5,935,163 A | 8/1999 | Gabbay | |
| 5,961,549 A | 10/1999 | Nguyen et al. | |
| 6,077,297 A | 6/2000 | Robinson et al. | |
| 6,083,257 A | 7/2000 | Taylor et al. | |
| 6,090,140 A | 7/2000 | Gabbay | |
| 6,214,036 B1 | 4/2001 | Letendre et al. | |
| 6,264,691 B1 | 7/2001 | Gabbay | |
| 6,267,783 B1 | 7/2001 | Letendre et al. | |
| 6,368,348 B1 | 4/2002 | Gabbay | |
| 6,419,695 B1 | 7/2002 | Gabbay | |
| 6,458,153 B1 | 10/2002 | Bailey et al. | |
| 6,468,660 B2 | 10/2002 | Ogle et al. | |
| 6,488,702 B1 | 12/2002 | Besselink | |
| 6,517,576 B2 | 2/2003 | Gabbay | |
| 6,533,810 B2 | 3/2003 | Hankh et al. | |
| 6,582,464 B2 | 6/2003 | Gabbay | |
| 6,610,088 B1 | 8/2003 | Gabbay | |
| 6,623,518 B2 | 9/2003 | Thompson et al. | |
| 6,685,625 B2 | 2/2004 | Gabbay | |
| 6,719,789 B2 | 4/2004 | Cox | |
| 6,730,118 B2 | 5/2004 | Spenser et al. | |
| 6,783,556 B1 | 8/2004 | Gabbay | |
| 6,790,230 B2 | 9/2004 | Beyersdorf et al. | |
| 6,814,746 B2 | 11/2004 | Thompson et al. | |
| 6,830,584 B1 | 12/2004 | Seguin | |
| 6,869,444 B2 | 3/2005 | Gabbay | |
| 6,893,460 B2 | 5/2005 | Spenser et al. | |
| 6,908,481 B2 | 6/2005 | Cribier | |
| 7,018,406 B2 | 3/2006 | Seguin et al. | |
| 7,025,780 B2 | 4/2006 | Gabbay | |
| 7,137,184 B2 | 11/2006 | Schreck | |
| 7,160,322 B2 | 1/2007 | Gabbay | |
| 7,247,167 B2 | 7/2007 | Gabbay | |
| 7,267,686 B2 | 9/2007 | DiMatteo et al. | |
| 7,311,730 B2 | 12/2007 | Gabbay | |
| 7,374,573 B2 | 5/2008 | Gabbay | |
| 7,381,218 B2 | 6/2008 | Schreck | |
| 7,452,371 B2 | 11/2008 | Pavcnik et al. | |
| 7,510,572 B2 | 3/2009 | Gabbay | |
| 7,524,331 B2 | 4/2009 | Birdsall | |
| RE40,816 E | 6/2009 | Taylor et al. | |
| 7,585,321 B2 | 9/2009 | Cribier | |
| 7,682,390 B2 | 3/2010 | Seguin | |
| 7,731,742 B2 | 6/2010 | Schlick et al. | |
| 7,803,185 B2 | 9/2010 | Gabbay | |
| 7,846,203 B2 | 12/2010 | Cribier | |
| 7,846,204 B2 | 12/2010 | Letac et al. | |
| 7,857,845 B2 | 12/2010 | Stacchino et al. | |
| 7,914,569 B2 | 3/2011 | Nguyen et al. | |
| D648,854 S | 11/2011 | Braido | |
| D652,926 S | 1/2012 | Braido | |
| D652,927 S | 1/2012 | Braido et al. | |
| D653,341 S | 1/2012 | Braido et al. | |
| D653,342 S | 1/2012 | Braido et al. | |
| D653,343 S | 1/2012 | Ness et al. | |
| D654,169 S | 2/2012 | Braido | |
| D654,170 S | 2/2012 | Braido et al. | |
| D660,432 S | 5/2012 | Braido | |
| D660,433 S | 5/2012 | Braido et al. | |
| D660,967 S | 5/2012 | Braido et al. | |
| D684,692 S | 5/2013 | Braido et al. | |
| 8,840,661 B2 | 9/2014 | Manasse | |
| 8,840,663 B2 | 9/2014 | Salahieh et al. | |
| 2002/0036220 A1 | 3/2002 | Gabbay | |
| 2003/0023303 A1 | 1/2003 | Palmaz et al. | |
| 2003/0050694 A1 | 3/2003 | Yang et al. | |
| 2003/0130726 A1 | 7/2003 | Thorpe et al. | |
| 2004/0049262 A1 | 3/2004 | Obermiller et al. | |
| 2004/0093075 A1 | 5/2004 | Kuehne | |
| 2004/0210304 A1 | 10/2004 | Seguin et al. | |
| 2005/0096726 A1 | 5/2005 | Sequin et al. | |
| 2005/0137695 A1 | 6/2005 | Salahieh et al. | |
| 2005/0137697 A1 | 6/2005 | Salahieh et al. | |
| 2005/0240200 A1 | 10/2005 | Bergheim | |
| 2005/0256566 A1 | 11/2005 | Gabbay | |
| 2006/0008497 A1 | 1/2006 | Gabbay | |
| 2006/0074484 A1 | 4/2006 | Huber | |
| 2006/0122692 A1 | 6/2006 | Gilad et al. | |
| 2006/0149360 A1 | 7/2006 | Schwammenthal et al. | |
| 2006/0173532 A1 | 8/2006 | Flagle et al. | |
| 2006/0178740 A1 | 8/2006 | Stacchino et al. | |
| 2006/0195180 A1 | 8/2006 | Kheradvar et al. | |
| 2006/0206202 A1 | 9/2006 | Bonhoeffer et al. | |
| 2006/0241744 A1 | 10/2006 | Beith | |
| 2006/0241745 A1 | 10/2006 | Solem | |
| 2006/0259120 A1 | 11/2006 | Vongphakdy et al. | |
| 2006/0259137 A1 | 11/2006 | Artof et al. | |
| 2006/0265056 A1 | 11/2006 | Nguyen et al. | |
| 2006/0276813 A1 | 12/2006 | Greenberg | |
| 2007/0010876 A1 | 1/2007 | Salahieh et al. | |
| 2007/0027534 A1 | 2/2007 | Bergheim et al. | |
| 2007/0043435 A1 | 2/2007 | Seguin et al. | |
| 2007/0050021 A1* | 3/2007 | Johnson ................ A61F 2/2412 623/2.14 |
| 2007/0055358 A1 | 3/2007 | Krolik et al. | |
| 2007/0067029 A1 | 3/2007 | Gabbay | |
| 2007/0093890 A1 | 4/2007 | Eliasen et al. | |
| 2007/0100435 A1 | 5/2007 | Case et al. | |
| 2007/0118210 A1 | 5/2007 | Pinchuk | |
| 2007/0213813 A1 | 9/2007 | Von Segesser et al. | |
| 2007/0233228 A1 | 10/2007 | Eberhardt et al. | |
| 2007/0244545 A1 | 10/2007 | Birdsall et al. | |
| 2007/0244552 A1 | 10/2007 | Salahieh et al. | |
| 2007/0288087 A1 | 12/2007 | Fearnot et al. | |
| 2008/0021552 A1 | 1/2008 | Gabbay | |
| 2008/0039934 A1 | 2/2008 | Styrc | |
| 2008/0071369 A1 | 3/2008 | Tuval et al. | |
| 2008/0082164 A1 | 4/2008 | Friedman | |
| 2008/0097595 A1 | 4/2008 | Gabbay | |
| 2008/0114452 A1 | 5/2008 | Gabbay | |
| 2008/0125853 A1 | 5/2008 | Bailey et al. | |
| 2008/0140189 A1 | 6/2008 | Nguyen et al. | |
| 2008/0147183 A1 | 6/2008 | Styrc | |
| 2008/0154355 A1 | 6/2008 | Benichou et al. | |
| 2008/0154356 A1 | 6/2008 | Obermiller et al. | |
| 2008/0243245 A1 | 10/2008 | Thambar et al. | |
| 2008/0255662 A1 | 10/2008 | Stacchino et al. | |
| 2008/0262602 A1 | 10/2008 | Wilk et al. | |
| 2008/0269879 A1 | 10/2008 | Sathe et al. | |
| 2009/0112309 A1 | 4/2009 | Jaramillo et al. | |
| 2009/0138079 A1 | 5/2009 | Tuval et al. | |
| 2010/0004740 A1 | 1/2010 | Seguin et al. | |
| 2010/0036484 A1 | 2/2010 | Hariton et al. | |
| 2010/0049306 A1 | 2/2010 | House et al. | |
| 2010/0087907 A1 | 4/2010 | Lattouf | |
| 2010/0131055 A1 | 5/2010 | Case et al. | |
| 2010/0168778 A1 | 7/2010 | Braido | |
| 2010/0168839 A1 | 7/2010 | Braido et al. | |
| 2010/0185277 A1 | 7/2010 | Braido et al. | |
| 2010/0191326 A1 | 7/2010 | Alkhatib | |
| 2010/0204781 A1 | 8/2010 | Alkhatib | |
| 2010/0204785 A1 | 8/2010 | Alkhatib | |
| 2010/0217382 A1 | 8/2010 | Chau et al. | |
| 2010/0249911 A1 | 9/2010 | Alkhatib | |
| 2010/0249923 A1 | 9/2010 | Alkhatib et al. | |
| 2010/0286768 A1 | 11/2010 | Alkhatib | |
| 2010/0298931 A1 | 11/2010 | Quadri et al. | |
| 2011/0029072 A1 | 2/2011 | Gabbay | |
| 2012/0303116 A1 | 11/2012 | Gorman, III et al. | |
| 2013/0023980 A1 | 1/2013 | Drasler | |
| 2016/0113764 A1 | 4/2016 | Sheahan et al. | |

(56) References Cited

U.S. PATENT DOCUMENTS

| | | | |
|---|---|---|---|
| 2016/0158013 A1 | 6/2016 | Carpentier et al. | |
| 2017/0216023 A1* | 8/2017 | Lane | A61F 2/2436 |

FOREIGN PATENT DOCUMENTS

| | | |
|---|---|---|
| DE | 102005003632 A1 | 8/2006 |
| DE | 202008009610 U1 | 12/2008 |
| EP | 0850607 A1 | 7/1998 |
| EP | 1000590 A1 | 5/2000 |
| EP | 1360942 B1 | 11/2003 |
| EP | 1584306 A1 | 10/2005 |
| EP | 1598031 A2 | 11/2005 |
| EP | 1 926 455 A2 | 6/2008 |
| FR | 2 847 800 B1 | 6/2004 |
| FR | 2850008 A1 | 7/2004 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 01028459 A1 | 4/2001 |
| WO | 0149213 A2 | 7/2001 |
| WO | 01054625 A1 | 8/2001 |
| WO | 01056500 A2 | 8/2001 |
| WO | 01076510 A2 | 10/2001 |
| WO | 0236048 A1 | 5/2002 |
| WO | 0247575 A2 | 6/2002 |
| WO | 02067782 A2 | 9/2002 |
| WO | 03047468 A1 | 6/2003 |
| WO | 2005070343 A1 | 8/2005 |
| WO | 06073626 A2 | 7/2006 |
| WO | 07071436 A2 | 6/2007 |
| WO | 08070797 A2 | 6/2008 |
| WO | 10/008549 A1 | 1/2010 |
| WO | 10008548 A2 | 1/2010 |
| WO | 10096176 A1 | 8/2010 |
| WO | 10098857 A1 | 9/2010 |

OTHER PUBLICATIONS

U.S. Appl. No. 29/375,243, Braido et al.
U.S. Appl. No. 29/375,260, filed Jun. 18, 2013, Braido et al.
"Closed heart surgery: Back to the future", Samuel V. Lichtenstein, The Journal of Thoracic and Cardiovascular Surgery, May 2006, vol. 131, No. 5, pp. 941-943.
"Direct-Access Valve Replacement", Christoph H. Huber, et al., Journal of the American College of Cardiology, vol. 46, No. 2, (Jul. 19, 2005).
"Minimally invasive cardiac surgery", M. J. Mack, Surgical Endoscopy, 2006, 20:S488-S492, DOI: 10.1007/s00464-006-0110-8 (presented Apr. 24, 2006).
"Percutaneous Aortic Valve Implantation Retrograde From the Femoral Artery", John G. Webb et al., Circulation, 2006; 113:842-850 (Feb. 6, 2006).
"Transapical aortic valve implantation: an animal feasibility study"; Todd M. Dewey et al., The annals of thoracic surgery 2006; 82: 110-6 (Feb. 13, 2006).
"Transapical approach for sutureless stent-fixed aortic valve implantation: experimental results"; Th. Walther et al., European Journal of Cardio-thoracic Surgery 29 (2006) 703-708 (Jan. 30, 2006).
"Transapical Transcatheter Aortic Valve Implantation in Humans", Samuel V. Lichtenstein et al., Circulation. 2006; 114: 591-596 (Jul. 31, 2006).
Catheter-implanted prosthetic heart valves, Knudsen, L.L., et al., The International Journal of Artificial Organs, vol. 16, No. 5 1993, pp. 253-262.
Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.
Percutaneous aortic valve replacement: resection before implantation, 836-840, Quaden, Rene et al., European J. of Cardio-thoracic Surgery, 27 (2005).
Ruiz, Carlos, Overview of PRE-CE Mark Transcatheter Aortic Valve Technologies, Euro PCR dated May 25, 2010.
Textbook "Transcatheter Valve Repair", 2006, pp. 165-186.
Transluminal Aortic Valve Placement, Moazami, Nader, et al., ASAIO Journal, 1996; 42:M381-M385.
Transluminal Catheter Implanted Prosthetic Heart Valves, Andersen, Henning Rud, International Journal of Angiology 7:102-106 (1998).
Transluminal implantation of artificial heart valves, Andersen, H. R., et al., European Heart Journal (1992) 13, 704-708.
U.S. Appl. No. 29/375,243, filed Sep. 20, 2010, titled "Surgical Stent Assembly.".

* cited by examiner

TRANSCATHETER MITRAL VALVE DESIGN

CROSS-REFERENCE TO RELATED APPLICATIONS

The present application claims priority to the filing date of U.S. Provisional Patent Application No. 62/466,423, filed on Mar. 3, 2017, the disclosure of which is hereby incorporated by reference herein.

BACKGROUND OF THE DISCLOSURE

The present disclosure relates to prosthetic heart valves and, in particular, collapsible prosthetic mitral valves.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

Prosthetic valves, particularly those for replacement of a native aortic valve, often contain three coapting leaflets as part of a valve assembly having a substantially circular or cylindrical shape, the valve assembly being supported by a substantially cylindrical stent. Although this type of prosthetic valve can be used to replace a native mitral valve, problems may arise from such use. For example, upon implantation in the native mitral valve annulus, a prosthetic heart valve with a cylindrical stent and cylindrical valve assembly having three leaflets may deform substantially to fit the elliptical geometry of the native mitral valve annulus. This deformation may prevent the three leaflets from properly coapting with one another to form a seal, which in turn may result in a greater degree of regurgitation (i.e., retrograde blood flow through the prosthetic valve). For this and other reasons, it would be desirable to have a prosthetic mitral valve better suited to the geometry of the native mitral valve.

BRIEF SUMMARY

According to one aspect of the disclosure, a prosthetic mitral valve includes a collapsible and expandable stent extending from an inflow end to an outflow end. A collapsible and expandable valve assembly is disposed within the stent, the valve assembly including a plurality of anterior leaflets each having a surface area and one posterior leaflet having a surface area. The surface area of the posterior leaflet is larger than the surface area of any of the anterior leaflets.

According to another aspect of the disclosure, a method of implanting a prosthetic mitral valve into a native mitral valve annulus of a patient includes delivering the prosthetic mitral valve in a collapsed condition to the native mitral valve annulus. The prosthetic mitral valve includes a collapsible and expandable stent and a valve assembly disposed within the stent. The valve assembly includes a plurality of anterior leaflets each having a surface area and one posterior leaflet having a surface area. The surface area of the posterior leaflet is larger than the surface area of any of the anterior leaflets. The method includes deploying the prosthetic mitral valve to an expanded condition within the native mitral valve annulus so that the anterior leaflets extend a lesser distance into a left ventricle of the patient than the posterior leaflet.

DETAILED DESCRIPTION

Blood flows through the mitral valve from the left atrium to the left ventricle. As used herein, the term "inflow end," when used in connection with a prosthetic mitral valve, refers to the end of the heart valve closest to the left atrium when the heart valve is implanted in a patient, whereas the term "outflow end," when used in connection with a prosthetic mitral valve, refers to the end of the heart valve closest to the left ventricle when the heart valve is implanted in a patient. As used herein, the terms "substantially," "generally," "approximately," and "about" are intended to mean that slight deviations from absolute are included within the scope of the term so modified. When ranges of values are described herein, those ranges are intended to include subranges. For example, a recited range of 1 to 10 includes 2, 5, 7, and other single values, as well as ranges of 2 to 6, 3 to 9, 4 to 5, and others.

Figure 1:
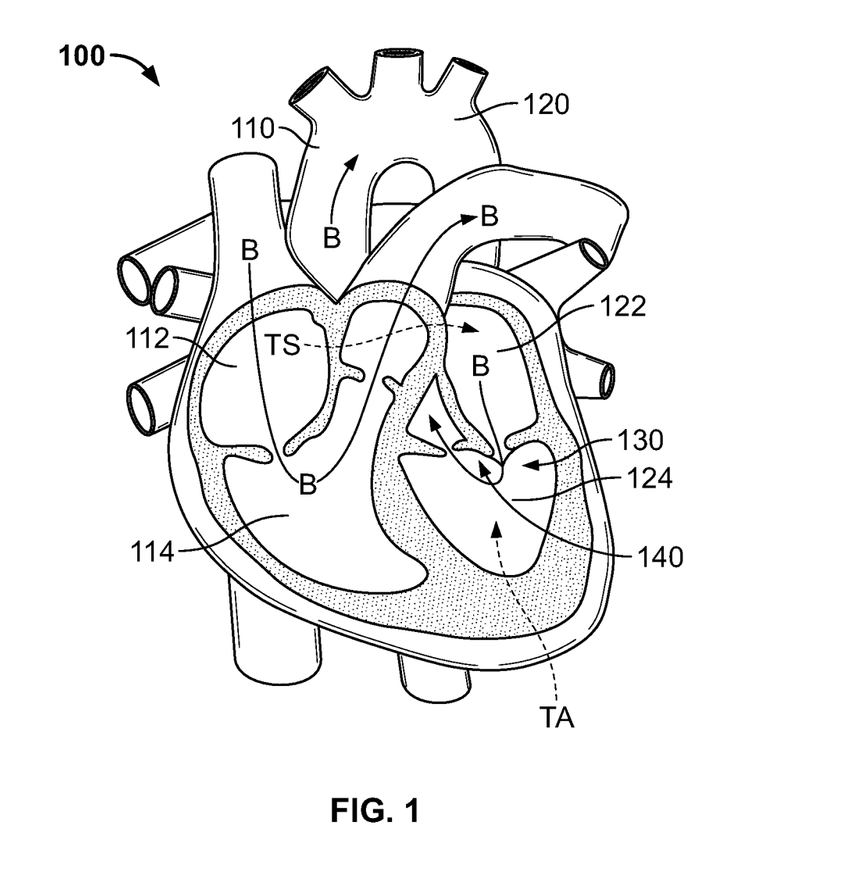
FIG. 1 is a highly schematic representation of a human heart.

FIG. 1 is a schematic representation of a human heart 100. The human heart includes two atria and two ventricles: a right atrium 112 and a left atrium 122, and a right ventricle 114 and a left ventricle 124. As illustrated in FIG. 1, the heart 100 further includes an aorta 110, and an aortic arch 120. Disposed between the left atrium 122 and the left ventricle 124 is the mitral valve 130. The mitral valve 130, also known as the bicuspid valve or left atrioventricular valve, is a dual-flap valve that opens as a result of increased pressure in the left atrium 122 as it fills with blood. As atrial pressure increases above that of the left ventricle 124, the mitral valve 130 opens and blood flows into the left ventricle. Similarly, disposed between aorta 110 and left ventricle 124 is the aortic valve 140. The aortic valve is a tricuspid valve that opens as a result of increased pressure in the left ventricle 124. Generally, the annulus of the aortic valve 140 is substantially circular or cylindrical, while the annulus of the mitral valve 130 is substantially elliptical. Blood flows through heart 100 in the direction shown by arrows "B".

An arrow labeled "TA" indicates a transapical approach of implanting a prosthetic heart valve, in this case to replace the mitral valve 130 of a patient. In transapical delivery, a small incision is made between the ribs and into the apex of the left ventricle 124 to deliver the prosthetic heart valve to the target site.

Figure 2:
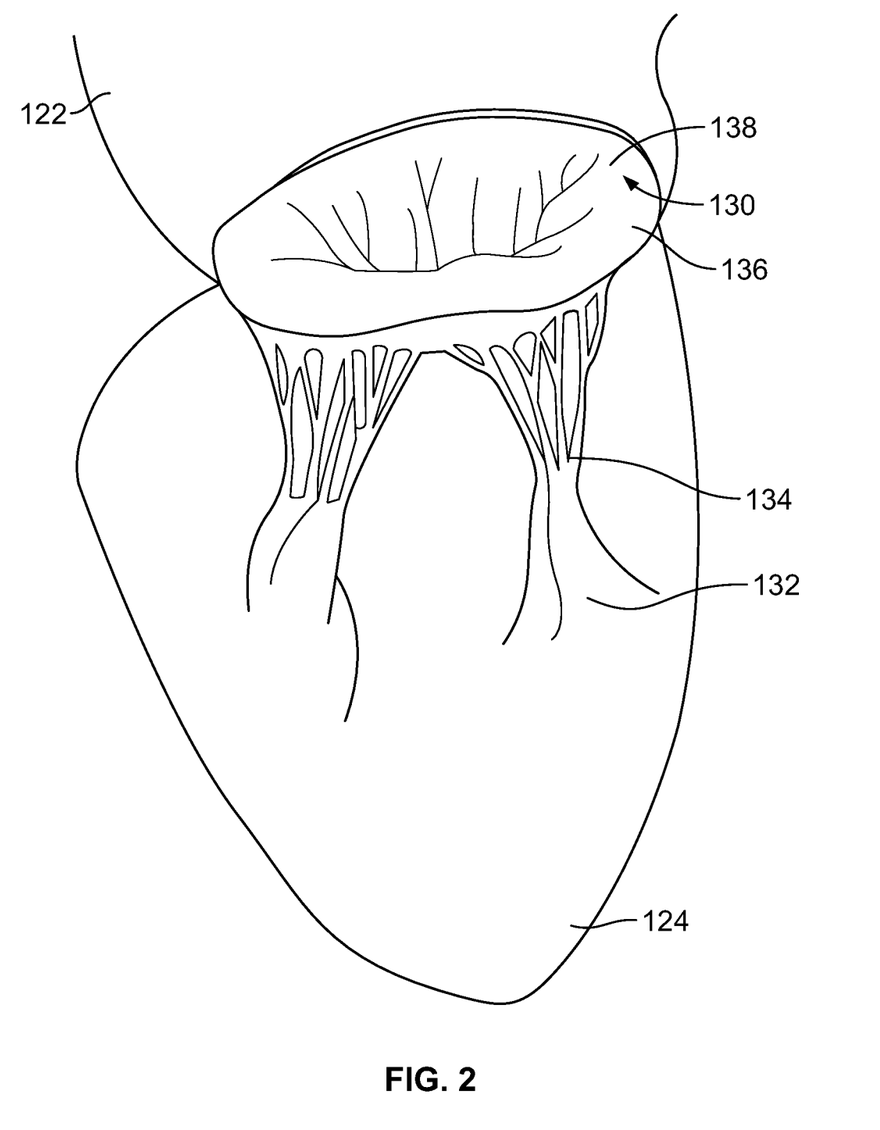
FIG. 2 is a highly schematic representation of a native mitral valve.

FIG. 2 is a more detailed schematic representation of native mitral valve 130 and its associated structures. As previously noted, mitral valve 130 includes two flaps or leaflets, a posterior leaflet 136 and an anterior leaflet 138, disposed between left atrium 122 and left ventricle 124. Anterior leaflet 138 is positioned relatively close to aortic valve 140, while posterior leaflet 136 is positioned relatively far from the aortic valve. Anterior leaflet 138 protrudes a greater length into left ventricle 124, while posterior leaflet 136 protrudes a relatively small distance into the left ventricle. Although posterior leaflet 136 is referred to as a single "leaflet," there are actually three scalloped sections of the posterior leaflet that coapt with anterior leaflet 138, which has a relatively smooth free edge. Cord-like tendons known as chordae tendineae 134 connect the two leaflets 136, 138 to the medial and lateral papillary muscles 132. During atrial systole, blood flows down the pressure gradient from the left atrium 122 to the left ventricle 124. When the left ventricle 124 contracts in ventricular systole, the increased blood pressure in the chamber pushes the leaflets 136 and 138 of the mitral valve 130 to close, preventing the backflow of blood into the left atrium 122. Since the blood pressure in the left atrium 122 is much lower than that in the left ventricle 124, the leaflets attempt to evert to the low pressure regions. The chordae tendineae 134 prevent the eversion by becoming tense, thus pulling on the leaflets and holding them in the closed position.

The goal of prosthetic heart valves is generally to provide a functional replacement for a malfunctioning native heart valve. Although the approach to creating such a prosthetic heart valve often relies on mimicking the structure of a healthy native valve, that approach may not always be optimal. For example, a prosthetic mitral valve that includes an anterior leaflet that extends a relatively great distance into left ventricle 124 may obstruct blood flowing from the left ventricle toward aorta 110. Further, supporting a long prosthetic anterior leaflet may require a correspondingly long support structure (such as a stent), and that support structure may contact the septal wall between left ventricle 124 and right ventricle 114 and cause ventricular fibrillation.

Figure 3:
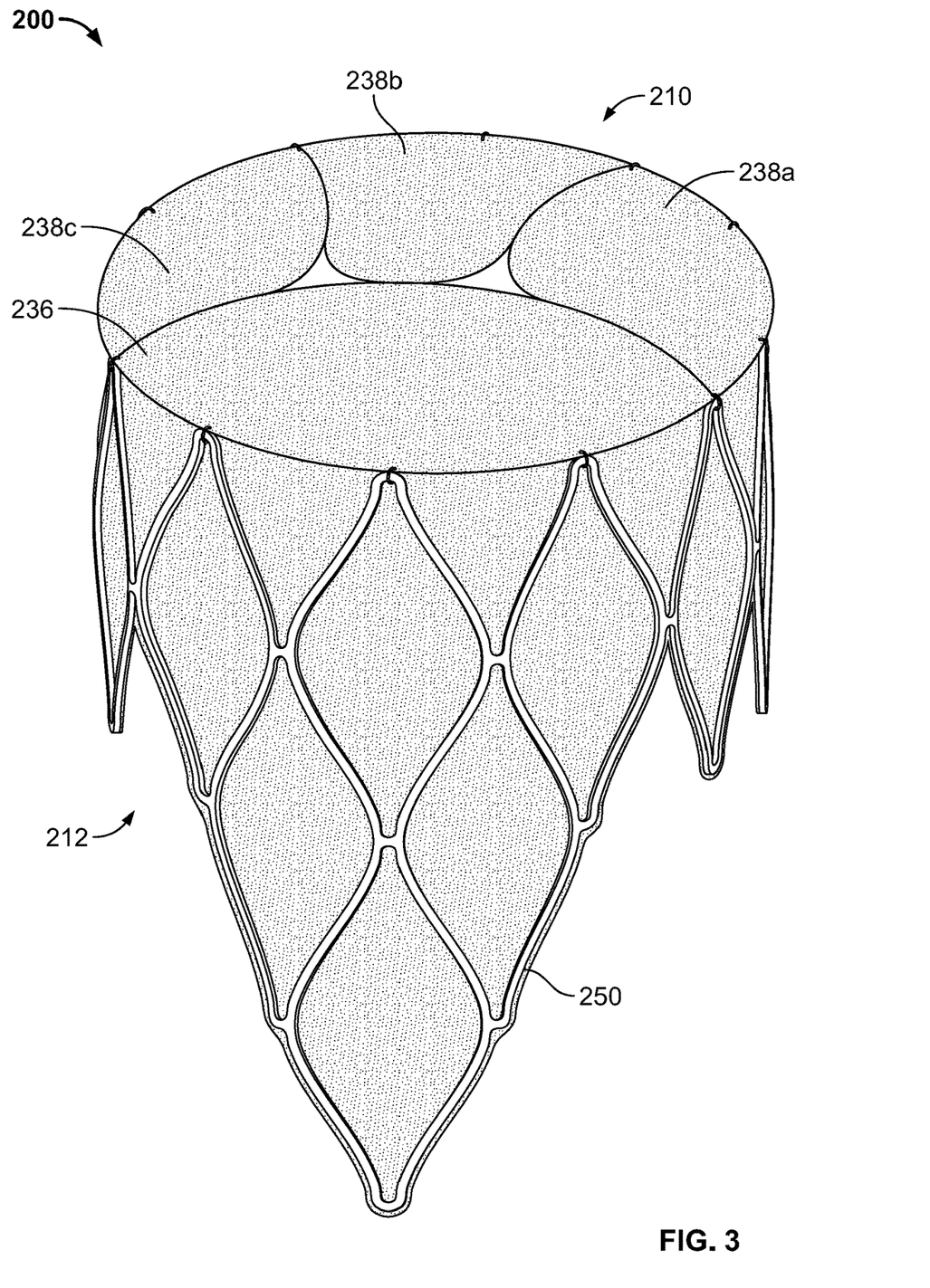
FIG. 3 is a highly schematic perspective view of a prosthetic mitral valve in an expanded condition according to an aspect of the disclosure.

A prosthetic mitral valve 200 that may address one or more of the issues addressed above is illustrated schematically in FIG. 3. Prosthetic heart valve 200 is a collapsible prosthetic heart valve designed to replace the function of the native mitral valve of a patient (see native mitral valve 130 of FIGS. 1-2). Generally, prosthetic valve 200 has an inflow end 210, an outflow end 212, and includes a plurality of leaflets attached to a support, the support being a collapsible and expandable stent 250 (best illustrated in FIGS. 4-5) in the illustrated embodiment. The prosthetic leaflets include a relatively large posterior leaflet 236 and three relatively small anterior leaflets 238a-c. Prosthetic valve 200 is illustrated in FIG. 3 in a coapted state in which the three anterior leaflets 238a-c coapt with one another and coapt with posterior leaflet 236 along a line of coaptation that is generally "C" or horseshoe-shaped. It should be noted that, although the native mitral valve includes a single large anterior leaflet 138, and a single posterior leaflet 136 with three sections (although some assert the posterior leaflet is actually three leaflets), these leaflet characteristics are reversed in prosthetic valve 200. FIG. 3 shows open space between adjacent coapted leaflets to better distinguish the leaflets in the drawings, but in practice little or no open space would remain between adjacent leaflets in the coapted state.

Figure 4:
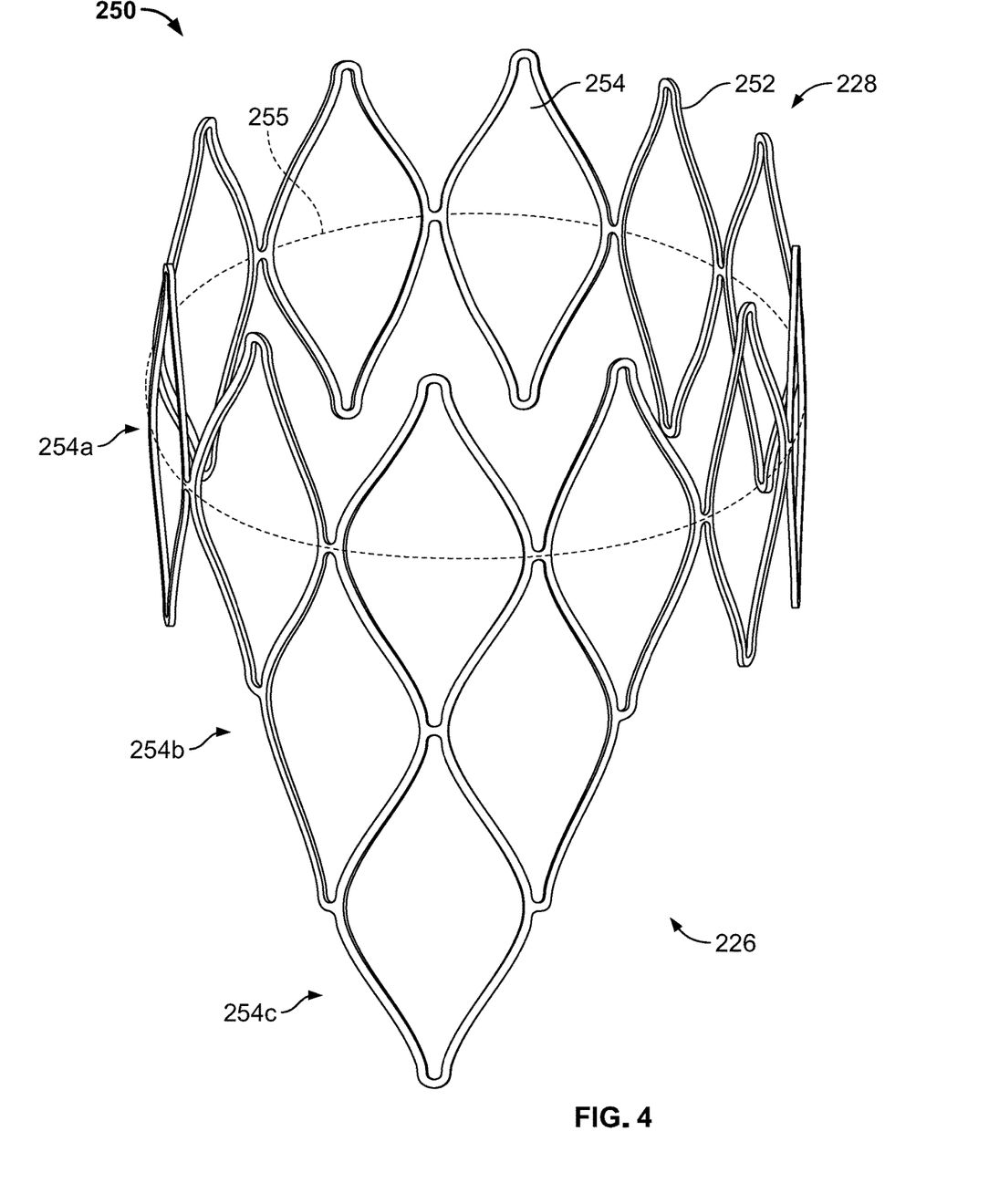
FIG. 4 is a highly schematic perspective view of a stent of the prosthetic mitral valve of FIG. 3.
Figure 5:
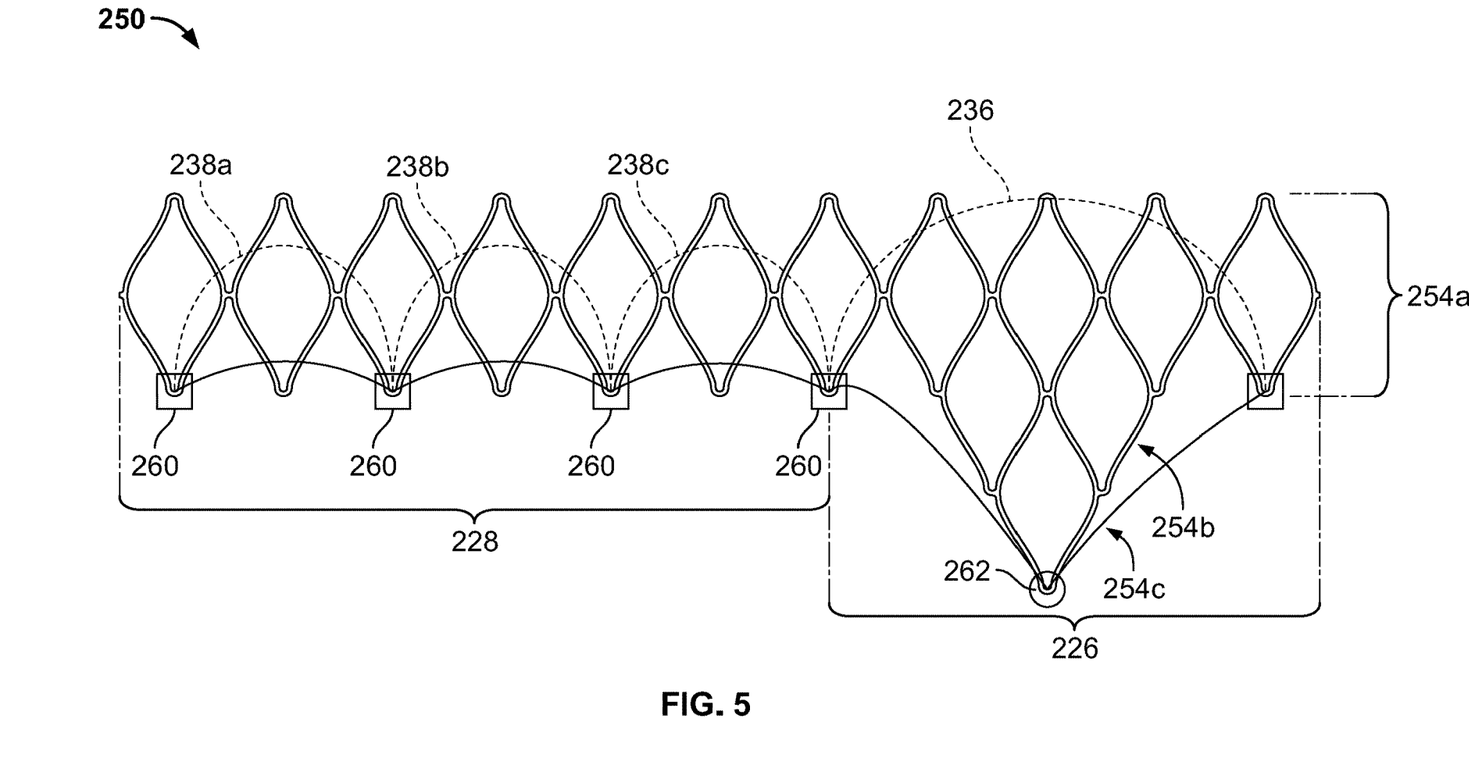
FIG. 5 is a highly schematic developed view of the stent of FIG. 4.

Stent 250 of prosthetic mitral valve 200 is illustrated in an expanded condition in FIG. 4, with other components of the prosthetic valve omitted for clarity. FIG. 5 illustrates stent 250 in a flattened or developed condition, as if cut longitudinally and unrolled onto a flat surface. FIG. 4 includes a dashed line 255 that is purely intended to aid in understanding the illustration and forms no part of the invention. Stent 250 may be formed from biocompatible materials that are capable of self-expansion, such as shape memory alloys including Nitinol. Stent 250 may include a plurality of struts 252 that form a plurality of closed cells 254 connected to one another in one or more annular rows around the stent. It should be understood that, in FIG. 5, the cells 254 at the left-most and right-most ends of the drawing are the same cell, with the cell being repeated to illustrate the continuity of the stent 250. Cells 254 may all be of substantially the same size around the perimeter and along the length of stent 250. In the illustrated embodiment, cells 254 are each substantially diamond-shaped in the expanded condition. Stent 250 may be radially expandable to provide a radial force to assist with positioning and stabilizing prosthetic heart valve 200 in the native valve annulus. Although stent 250 is illustrated as having a substantially circular profile, it should be understood that the stent may alternatively have an elliptical profile or a "D"-shaped profile in the expanded condition to better match the shape of the annulus of native mitral valve 130.

Stent 250 includes an anterior section 228 adapted to support anterior leaflets 238a-c and a posterior section 226 adapted to support posterior leaflet 236. In the view of FIG. 4, the anterior direction is into the page and the posterior direction is out of the page. Stent 250 may include a single annular row of cells 254a connected to one another around the entire circumference of the stent, represented by the dashed line 255 of FIG. 4. The anterior section 228 of stent 250 may be limited to a single row of cells 254a with no additional cells 254 being present. The posterior section 226 of stent 250, on the other hand, may include cells 254a as well as additional cells 254 to support the larger posterior leaflet 236. In the illustrated embodiment, posterior section 226 includes a second row of cells 254b extending in the outflow direction from the first row of cells 254a. As illustrated, second row of cells 254b includes two cells 254, although the second row may include additional cells. However, second row of cells 254b preferably is limited to posterior section 226 and does not extend circumferentially to anterior section 228. Posterior section 226 may also include a third row of cells 254c extending in the outflow direction from the second row of cells 254b. In the illustrated embodiment, the third row of cells 254c includes a single cell 254, although the third row may include additional cells. However, similar to second row of cells 254b, third row of cells 254c preferably is limited to posterior section 226 and does not extend to anterior section 228. If cells 254 are all of substantially the same size, the first row 254a preferably includes more cells than the second row 254b, which in turn preferably includes more cells than the third row 254c.

The posterior leaflet 236 and anterior leaflets 238a-c may be attached to stent 250 via a commissure attachment features ("CAF") 260. One pair of circumferentially adjacent CAFs 260 may be used to attach posterior leaflet 236 to stent 250, and another pair of circumferentially adjacent CAFs 260 may be used to attach anterior leaflets 238a-c to stent 250. CAFs 260 are preferably positioned at the outflow end 212 of a cell 254, and include one or more apertures or eyelets to accept sutures or other devices for attaching the leaflets to stent 250. Prior to describing the attachment of anterior leaflets 238a and posterior leaflet 236 to stent 250, an exemplary anterior leaflet is described.

Figure 6:
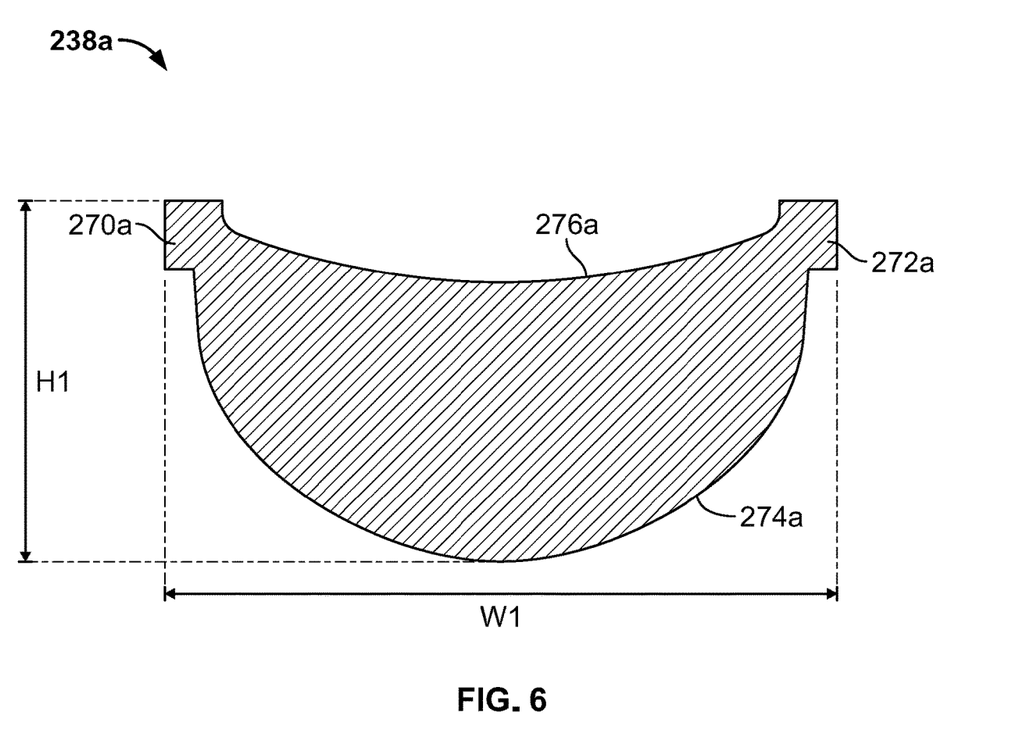
FIG. 6 is a plan view of an anterior leaflet of the prosthetic mitral valve of FIG. 3.

One anterior leaflet 238a of prosthetic valve 200 is illustrated in a flattened condition in FIG. 6. Anterior leaflets 238b-c may be similar, identical or substantially identical to anterior leaflet 238a. Generally, anterior leaflet 238a includes a first edge 274a having a generally arcuate shape and a second or free edge 276a, which may have a less pronounced arcuate shape than the first edge. A first tab 270a may connect the ends of first edge 274a and second edge 276a on one end of the leaflet, and a second tab 272a may connect the ends of first edge 274a and second edge 276a on the other end of the leaflet. Tabs 270a and 272a may be at least partially rectangular and provide a surface for attachment to stent 250. Each anterior leaflet, including anterior leaflet 238a, may have a height H1 from the top of tabs 270a, 272a to the bottom of first edge 274a (as seen in FIG. 6). Similarly, each anterior leaflet, including anterior leaflet 238a, may have a width W1 from the outer lateral edge of tab 270a to the outer lateral edge of tab 272a.

Figure 7:
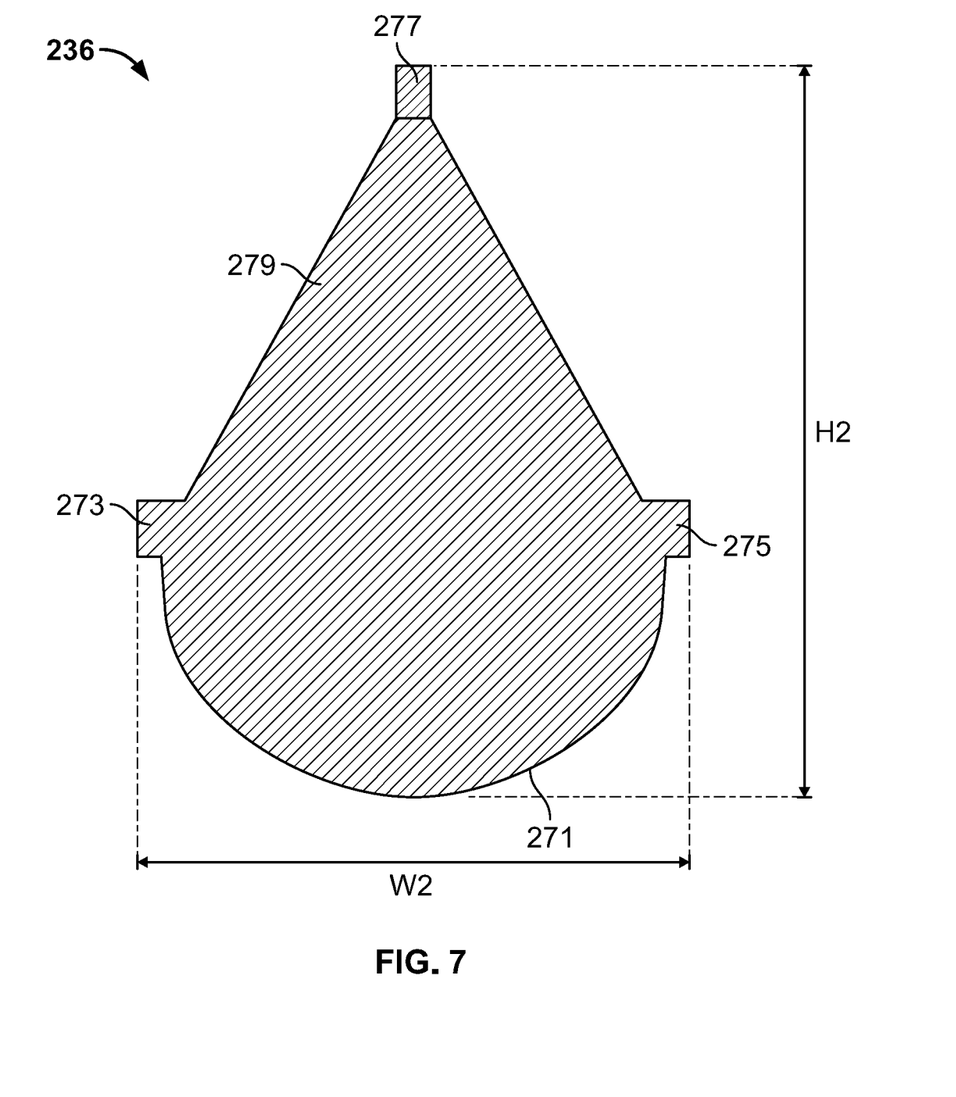
FIG. 7 is a plan view of a posterior leaflet of the prosthetic mitral valve of FIG. 3.

Posterior leaflet 236 of prosthetic valve 200 is illustrated in a flattened condition in FIG. 7. Generally, posterior leaflet 236 includes a first edge 271 having a generally arcuate shape, with the first edge extending from a first tab 273 to a second tab 275, both of which may include rectangular portions. A tapered portion 279 may include two substantially straight edges that extend from the first tab 273 and second tab 275, respectively, and meet one another at a third tab 277, which may also be substantially rectangular. With this configuration, tapered portion 279 is relatively wide adjacent tabs 273 and 275, with the width decreasing in the direction of third tab 277. Posterior leaflet 236, may have a height H2 from the top of tab 277 to the bottom of first edge 271 (as seen in FIG. 7), and a width W2 from the outer lateral edge of tab 273 to the outer lateral edge of tab 275. The height H2 of posterior leaflet 236 is greater than the height H1 of each anterior leaflet 238a-c, and the width W2 of the posterior leaflet is greater than the width W1 of each anterior leaflet. As a result, the surface area of posterior leaflet 236 is greater than the surface area of each anterior leaflet 238a-c.

Referring back to FIG. 5, each tab of each anterior leaflet 238a-c may be attached to a tab of an adjacent leaflet at one of the CAFs 260 on anterior section 228 of stent 250. The first edge of each anterior leaflet may be coupled to stent 250 via a cuff (not shown) attached to the stent. The cuff may be disposed on the lumenal surface of stent 250, the ablumenal surface, or both surfaces. The cuff may be wholly or partly formed from any suitable biological material, such as bovine or porcine pericardium, or from one or more polymers, such as polytetrafluoroethylene (PTFE), urethanes and the like. For the embodiment of stent 250 illustrated in FIGS. 4-5, the cuff preferably covers most or all of the open space within cells 254. The dashed lines of FIG. 5 illustrate the lines along which the first edge of each leaflet is attached to the cuff. For example, the first edge of each leaflet may be sutured to the cuff, and also to stent 250 if desired, by passing strings or sutures through the cuff and around struts 252. The second or free edge of each anterior leaflet 238a-c may coapt with the free edge of adjacent anterior leaflets. The first edge 271 of posterior leaflet 236 may similarly be attached to stent 250, for example via the cuff, with tabs 273 and 275 coupled to adjacent CAFs 260 on posterior section 226 of stent 250. The third tab 277 of posterior leaflet 236 may be attached to stent 250 at an attachment location 262. Attachment location 262 may take the form of a CAF similar to CAFs 260, or any may take other suitable form. For example, attachment location 262 may simply be the apex of a cell 254, such as the single cell in third row 254c, at which two struts 252 meet one another.

Referring again to FIG. 6, each anterior leaflet 238a-c may be fully supported by stent 250 by the connection of its tabs, such as tabs 270a and 272a, to corresponding CAFs 260, as well as the attachment of its first edge to the cuff. In other words, when prosthetic heart valve 200 is implanted into a native mitral valve annulus, anterior leaflets 238a-c may coapt with one another and/or with posterior leaflet 236 to stop blood from flowing in the retrograde direction from left ventricle 124 to left atrium 122, without the anterior leaflets everting or otherwise malfunctioning. However, because posterior leaflet 236 is substantially larger than each of the anterior leaflets 238a-c, relatively large forces may be applied to the posterior leaflet as it coapts with the anterior leaflets to resist retrograde blood flow. In native mitral valve 130, as described above, anterior leaflet 138 and posterior leaflet 136 are each attached to papillary muscles 132 via chordae tendinae 134, which helps resist leaflet eversion. The attachment of third tab 277 of posterior leaflet 236 to attachment location 262 may provide similar eversion resistance for the posterior leaflet 236, without requiring any connection between the posterior leaflet and native anatomy, such as chordae tendinae 134 or papillary muscles 132.

Although the particular size of posterior leaflet 236 compared to the size of anterior leaflets 238a-c may vary, certain relative sizes may be preferable. For example, when posterior leaflet 236 and anterior leaflets 238a-c are in the coapted condition, if the area of the leaflets were projected onto the circle (or ellipse, D-shape, etc.) formed by stent 250, the projected area of posterior leaflet 236 would preferably occupy between about 50% and about 60% of the total area, while the anterior leaflets 238a-c would preferably occupy between about 40% and about 50% of that area. In the scenario in which each anterior leaflet 238a-c is identical or similar, the projected area of each individual anterior leaflet 238a-c preferably would occupy between about 13% and about 17% of the area defined by the circumference of stent 250. Another relative measure of the size of posterior leaflet 236 compared to anterior leaflets 238a-c may be in reference to the distance of the interior circumference of stent 250 occupied by each leaflet. For example, referring to FIG. 5, each anterior leaflet 238a-c may span the circumference of about two cells 254. Posterior leaflet 236 may span the circumference of about four cells 254. Because each cell 254 is about the same size in FIG. 5, each anterior leaflet 238a-c spans about 20% of the interior circumference of stent 250, while posterior leaflet 236 spans about 40% of the interior circumference of the stent.

Figure 8:
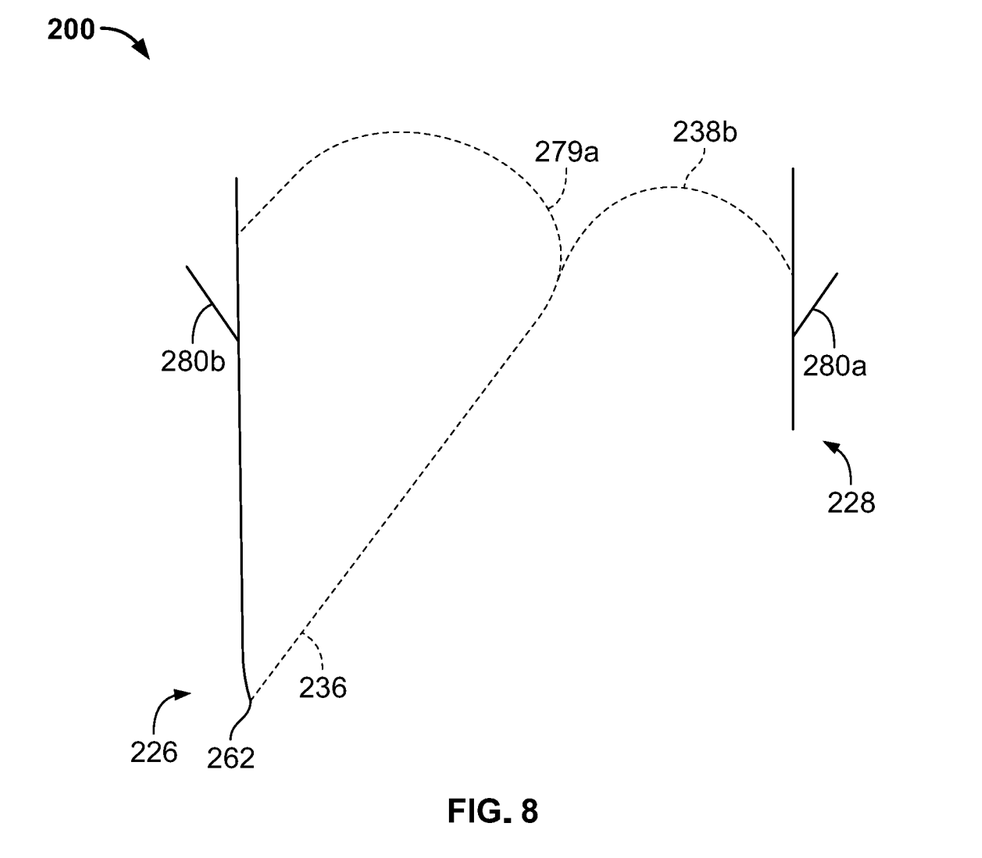
FIG. 8 is a highly schematic longitudinal cross-section of the prosthetic mitral valve of FIG. 3 with the leaflets in a coapted condition.

FIG. 8 illustrates a schematic cross-section of prosthetic heart valve 200 with the leaflets in a coapted state. In FIG. 8, posterior leaflet 236 and anterior leaflet 238b are shown, but it should be understood that anterior leaflets 238a and 238c would also be coapting with adjacent leaflets to prevent retrograde blood flow. Despite tapered portion 279 being coupled to attachment location 262 via third tab 277, posterior leaflet 236 retains enough slack between first edge 271 and third tab 277 to form a billowing portion 279a which coapts with anterior leaflets 238a-c. In some embodiments, stent 250 may include anchor features, such as anterior anchor 280a to clip over the native anterior leaflet 138 and posterior anchor 280b to clip over the native posterior leaflet 136. Anchor features 280a-b may take any suitable form, including struts integral with stent 250, with free ends that are biased outward in the absence of an applied force, with the anchor features being transitionable to a nested condition within a cell 254 when prosthetic heart valve 200 is in a collapsed condition. With this configuration, anchor features 280a-b may be substantially flush with the remainder of stent 250 during delivery, and upon expansion to the expanded condition, the free ends of anchor features 280a-b may transition radially outwardly so that native mitral valve leaflets 136, 138 may be sandwiched between anchor features 280a-b and the remainder of stent 250.

In order to implant prosthetic heart valve 200 into the native mitral valve annulus of a patient, the valve 200, including stent 250 and leaflets 236 and 238a-c, may be crimped to a collapsed condition, loaded into a delivery device (not shown), and covered by a sheath of the delivery device to maintain the valve in the collapsed condition. The delivery device is then advanced to the annulus of the native mitral valve 130, for example through the vasculature via an opening in the femoral artery (transfemoral delivery), or through an incision in the apex of left ventricle 124 (transapical delivery). Other delivery methods, such as transseptal delivery, are also contemplated herein. Once the sheath is positioned at the desired location with respect to the native mitral valve annulus, which may be confirmed by imaging techniques such as fluoroscopy, the sheath may be advanced or retracted relative to the remainder of the delivery device to expose prosthetic heart valve 200. As the sheath is moved from around prosthetic heart valve 200, constrictive forces are removed from the valve, which begins to expand as stent 250 begins to return to its set shape (i.e., the expanded condition). Upon implantation, the inflow end 210 of stent 250 and the first edges of each leaflet 236, 238a-c are oriented toward left atrium 122 while the outflow end 212 of stent 250 and the free edges of each anterior leaflet 238a-c and the tapered portion 279 of posterior leaflet 236 are oriented toward left ventricle 124. If prosthetic heart valve 200 includes anchor features 280a-b, the native posterior leaflet 136 and anterior leaflet 138 may be sandwiched between the anchor features and stent 250 to help stabilized the prosthetic valve within the native mitral valve 130.

It is desirable that prosthetic valve 200, upon implantation, be oriented such that anterior leaflets 238a-c are positioned nearer native aortic valve 140, and posterior leaflet 236 is positioned farther away from the native aortic valve. As the anterior section 228 of stent 250 and anterior leaflets 238a-c do not extend a substantial distance into left ventricle 124, this configuration may provide at least two benefits. First, the shallow anterior section of the prosthetic heart valve 200 may reduce the likelihood that any structure of prosthetic heart valve will contact the septum separating left ventricle 124 from right ventricle 114, which could cause ventricular fibrillation. Second, the shallow anterior section of prosthetic heart valve 200 may reduce the likelihood of any structure of the prosthetic heart valve obstructing blood flow from the left ventricle to aorta 110 through aortic valve 140. The relatively large posterior leaflet 236, on the other hand, is positioned away from the native aortic valve 140 and the septum separating left ventricle 124 from right ventricle 114. The associated larger size of the posterior portion 226 of stent 250 is also positioned away from native aortic valve 140, reducing the likelihood of interference with the native anatomy.

According to one embodiment of the disclosure, a prosthetic mitral valve comprises:

a collapsible and expandable stent extending from an inflow end to an outflow end; and a collapsible and expandable valve assembly disposed within the stent, the valve assembly including a plurality of anterior leaflets each having a surface area and one posterior leaflet having a surface area, the surface area of the posterior leaflet being larger than the surface area of any of the anterior leaflets; and/or the surface area of each anterior leaflet is about the same; and/or each anterior leaflet has a first edge coupled to the stent and a free edge nearer the outflow end of the stent than the inflow end of the stent; and/or the posterior leaflet has a first edge coupled to the stent adjacent the inflow end of the stent; and/or the posterior leaflet includes a tapered portion extending away from the first edge, the tapered portion having a width that decreases in a direction from the inflow end of the stent toward the outflow end of the stent; and/or the tapered portion of the posterior leaflet is coupled to the stent adjacent the outflow end of the stent; and/or the stent includes an anterior section, a posterior section, a first circumferential row of cells, and a second row of cells coupled to the first row of cells, the first row of cells being positioned in the anterior section and the posterior section of the stent, the second row of cells being positioned only in the posterior section of the stent; and/or the posterior section includes a third row having at least one cell coupled to the second row of cells; and/or the third row includes a single cell; and/or the posterior leaflet includes a first edge coupled to the stent adjacent the inflow end of the stent, and a second end opposite the first edge coupled to the single cell in the third row; and/or the plurality of anterior leaflets includes exactly three anterior leaflets.

In another embodiment of the disclosure, a method of implanting a prosthetic mitral valve into a native mitral valve annulus of a patient comprises:

delivering the prosthetic mitral valve in a collapsed condition to the native mitral valve annulus, the prosthetic mitral valve including a collapsible and expandable stent and a valve assembly disposed within the stent, the valve assembly including a plurality of anterior leaflets each having a surface area and one posterior leaflet having a surface area, the surface area of the posterior leaflet being larger than the surface area of any of the anterior leaflets; and deploying the prosthetic mitral valve to an expanded condition within the native mitral valve annulus so that the posterior leaflet extends a greater distance into a left ventricle of the patient than any of the anterior leaflets; and/or the surface area of each of the anterior leaflets is about the same; and/or each anterior leaflet has a first edge coupled to the stent and a free edge nearer an outflow end of the stent than an inflow end of the stent; and/or the posterior leaflet has a first edge coupled to the stent adjacent an inflow end of the stent; and/or the posterior leaflet includes a tapered portion extending away from the first edge, the tapered portion having a width that decreases in a direction from the inflow end of the stent toward an outflow end of the stent; and/or the tapered portion of the posterior leaflet is coupled to the stent adjacent the outflow end of the stent; and/or the stent includes an anterior section, a posterior section, a first circumferential row of cells, and a second row of cells coupled to the first row of cells, the first row of cells being positioned in the anterior section and the posterior section of the stent, the second row of cells being positioned only in the posterior section of the stent; and/or the posterior section includes a third row having at least one cell coupled to the second row of cells; and/or the third row includes a single cell; and/or the posterior leaflet includes a first edge coupled to the stent adjacent the inflow end of the stent, and a second end opposite the first edge coupled to the single cell in the third row; and/or the deploying step includes deploying the prosthetic valve so that the anterior leaflets are positioned closer to a native aortic valve than the posterior leaflet.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, features of one embodiment of the invention may be combined with features of one or more other embodiments of the invention without departing from the scope of the invention.

The invention claimed is:

1. A prosthetic mitral valve, comprising:
   a collapsible and expandable stent extending from an inflow end to an outflow end, the stent including an anterior section and a posterior section; and
   a collapsible and expandable valve assembly disposed within the stent, the valve assembly including a plurality of anterior leaflets each having a surface area and one posterior leaflet having a surface area, the surface area of the posterior leaflet being larger than the surface area of any of the anterior leaflets,
   wherein a first entire length of the stent between the inflow end and the outflow end at the posterior section of the stent is larger than a second entire length of the stent between the inflow end and the outflow end at the anterior section of the stent, the first entire length being adapted to support the larger surface area of the posterior leaflet,
   wherein, in an implanted condition of the prosthetic mitral valve, the one posterior leaflet of the valve assembly is configured to be positioned at a posterior side of a native mitral valve annulus, and the plurality of anterior leaflets of the valve assembly is configured to be positioned at an anterior side of the native mitral valve annulus, so that the one posterior leaflet is positioned farther away from a native aortic valve than is the plurality of anterior leaflets.

2. The prosthetic mitral valve of claim 1, wherein the surface area of each anterior leaflet is about the same.

3. The prosthetic mitral valve of claim 1, wherein each anterior leaflet has a first edge coupled to the stent and a free edge nearer the outflow end of the stent than the inflow end of the stent.

4. The prosthetic mitral valve of claim 1, wherein the posterior leaflet has a first edge coupled to the stent adjacent the inflow end of the stent.

5. The prosthetic mitral valve of claim 4, wherein the posterior leaflet includes a tapered portion extending away from the first edge, the tapered portion having a width that decreases in a direction from the inflow end of the stent toward the outflow end of the stent.

6. The prosthetic mitral valve of claim 5, wherein the tapered portion of the posterior leaflet is coupled to the stent adjacent the outflow end of the stent.

7. The prosthetic mitral valve of claim 1, wherein the stent includes a first circumferential row of cells, and a second row of cells coupled to the first row of cells, the first row of cells being positioned in the anterior section and the posterior section of the stent, the second row of cells being positioned only in the posterior section of the stent.

8. The prosthetic mitral valve of claim 7, wherein the posterior section includes a third row having at least one cell coupled to the second row of cells.

9. The prosthetic mitral valve of claim 8, wherein the third row includes a single cell.

10. The prosthetic mitral valve of claim 9, wherein the posterior leaflet includes a first edge coupled to the stent adjacent the inflow end of the stent, and a second end opposite the first edge coupled to the single cell in the third row.

11. The prosthetic mitral valve of claim 1, wherein the plurality of anterior leaflets includes exactly three anterior leaflets.

* * * * *